United States Patent [19]
Nave

[11] Patent Number: 5,783,152
[45] Date of Patent: Jul. 21, 1998

[54] THIN-FILM FIBER OPTIC HYDROGEN AND TEMPERATURE SENSOR SYSTEM

[75] Inventor: Stanley E. Nave, Evans, Ga.

[73] Assignee: The United States of America as represented by the United States Department of Energy, Washington, D.C.

[21] Appl. No.: 824,063

[22] Filed: Mar. 24, 1997

[51] Int. Cl.$^6$ ............................................. G01N 21/75
[52] U.S. Cl. .............................. 422/82.06; 422/82.12; 436/144
[58] Field of Search ..................... 422/82.05, 82.06, 422/82.09, 82.12; 436/144, 164

[56] References Cited

U.S. PATENT DOCUMENTS

| | | | |
|---|---|---|---|
| 5,322,798 | 6/1994 | Sadowski | 422/82.05 |
| 5,404,218 | 4/1995 | Nave et al. | 356/301 |
| 5,637,507 | 6/1997 | Wicks et al. | 436/166 |

OTHER PUBLICATIONS

Frazier, G. A. "Thermoreflectance of palladium hydride" AIP Conference Proceedings, No. 40, (1978), pp. 342–347 1978.

Kazansky, V.B. et al "The unusual properties of small platinum particles supported on basic carriers" Stud Surf. Sci. Catal. vol. 92 (1994)pp. 275–280 1994.

Majkrzak, C.F. et al "Determination of hydrogen(deuterium) density profiles in thin metal films and multilayers by neutron reflection" Mater. Res. Soc. Symp. Proc., vol. 166, (1990) pp. 127–132 1990.

*Primary Examiner*—Jeffrey Snay
*Attorney, Agent, or Firm*—Harold M. Dixon; William R. Moser; Paul A. Gottlieb

[57] ABSTRACT

The invention discloses a sensor probe device for monitoring of hydrogen gas concentrations and temperatures by the same sensor probe. The sensor probe is constructed using thin-film deposition methods for the placement of a multitude of layers of materials sensitive to hydrogen concentrations and temperature on the end of a light transparent lens located within the sensor probe. The end of the lens within the sensor probe contains a lens containing a layer of hydrogen permeable material which excludes other reactive gases, a layer of reflective metal material that forms a metal hydride upon absorbing hydrogen, and a layer of semiconducting solid that is transparent above a temperature dependent minimum wavelength for temperature detection. The three layers of materials are located at the distal end of the lens located within the sensor probe. The lens focuses light generated by broad-band light generator and connected by fiber-optics to the sensor probe, onto a reflective metal material layer, which passes through the semi-conducting solid layer, onto two optical fibers located at the base of the sensor probe. The reflected light is transmitted over fiberoptic cables to a spectrometer and system controller. The absence of electrical signals and electrical wires in the sensor probe provides for an elimination of the potential for spark sources when monitoring in hydrogen rich environments, and provides a sensor free from electrical interferences.

13 Claims, 2 Drawing Sheets

THIN-FILM FIBER OPTIC HYDROGEN AND TEMPERATURE SENSOR SYSTEM

The United States Government has rights in this invention pursuant to Contract No. DE-AC09-89-SR18035 between the U.S. Department of Energy and Westinghouse Savannah River Company.

DISCLOSURE

The present invention relates to the monitoring of hydrogen gas concentrations and temperatures by the same sensor probe. The present invention utilizes hydrogen-absorbing materials as disclosed in U.S. patent application No. 08/192,266, by Wicks, et al., filed Feb. 7, 1994, titled, "Tetraethyl OrthosilicateBased Glass Composition and Method," now U.S. 5,637,507, and included herein by reference.

BACKGROUND OF THE INVENTION

1. Field of the Invention

The invention relates generally to a sensor system that combines thin-film technology and different composite materials in three layers at the end of a sensor probe to provide the ability to monitor for hydrogen gas concentrations, and the ability to monitor for temperature. The sensor probe provides safe and efficient transmission of hydrogen gas concentrations and temperature information by fiber optic cables to equipment for analysis.

2. Description of Related Art

Monitoring the concentrations of hydrogen gas concentrations in hydrogen enriched environments has been accomplished with separate probes and sensors that are electrically powered. The sensors typically have electrical connections that may create sparking situations when measuring in explosive gas environments.

Fiber optics have previously been utilized to sequentially transmit information accumulated by temperature probes, or separate gas concentration sensors. For the foregoing reasons, there is a need for an apparatus that is small, light-weight, capable of monitoring for temperatures and for hydrogen concentrations, and which does not generate electrical interference signals or the potential for electrical sparks. There is much room for improvement in the art, as suggested below.

SUMMARY OF THE INVENTION

It is an object of this invention to provide an apparatus and process that provides for the safe and efficient real-time simultaneously monitoring of hydrogen gas concentrations and temperature in confined spaces or offgas streams.

It is a further object of this invention to provide an apparatus and process to obtain reliable assessment of the concentration of hydrogen gas in enclosed spaces or offgas streams with a sensor system and probe that does not provide an electrical sparking hazard.

It is a further and more particular object of this invention to provide an apparatus and process which enables one to obtain reliable temperature readings, preferably with the same probe.

It is yet a further more particular object of this invention to provide an apparatus and process which enables the monitoring of reliable readings of hydrogen gas concentrations and temperatures which are not subject to electrical interference.

It is an additional object of this invention to provide a novel sensor system and probe which is light-weight, of sturdy construction, and has exterior surfaces which resist mechanical or chemical deterioration.

These and other objects of the invention are accomplished by a sensor system comprising a sensor probe containing a quartz lens, a cylindrical enclosure, with three layers of material deposited on the distal end of the sensor probe. The three layers of materials at the end include an exterior layer of a hydrogen permeable coating, a middle layer of reflective metal material that forms a metal hydride upon absorbing hydrogen, and a semi-conducting solid that is transparent above a temperature dependent minimum wave length, which is the interior layer contiguous with a quartz lens that fills most of the cylindrical enclosure of the sensor probe. The interior end of the quartz lens is in close proximity to the base of the sensor probe, which houses a fiber-optic cable connector that positions two optic fibers at the focal point of the quartz lens, and which transmit light to and from the quartz lens. The fiber optic cable connects the sensor probe to the broad band light generating system. The light generated by the light source is directed through the cable to the quartz lens and to the reflective metal material that forms a metal hydride upon absorbing hydrogen, which is located in the distal end of the sensor probe.

The light reflected by the reflective metal material layer, and the altered light passing through the semi-conducting solid layer that is transparent to light depending on the temperature, is conveyed by fiber optic cable to a diode array spectrometer, with analysis provided by an analog to a digital converter and a system controlling software that provides real-time output of hydrogen concentrations and temperature readings. The hydrogen concentrations and temperature readings are monitored simultaneously and continuously at the distal end of the sensor probe. Thus, the objects of the invention are accomplished by the sensor probe system described herein.

BRIEF DESCRIPTION OF THE DRAWINGS

These and other features, aspects, and advantages of this invention will be better understood with regard to the following description, appended claims, and accompanying drawings where:

DETAILED DESCRIPTION

Figure 1:
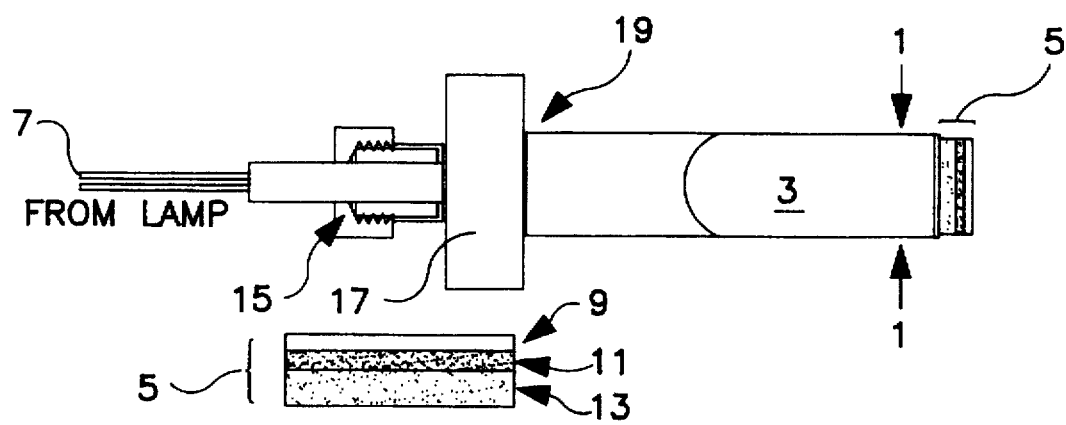
FIG. 1, is a cross-section of the sensor.
Figure 2:
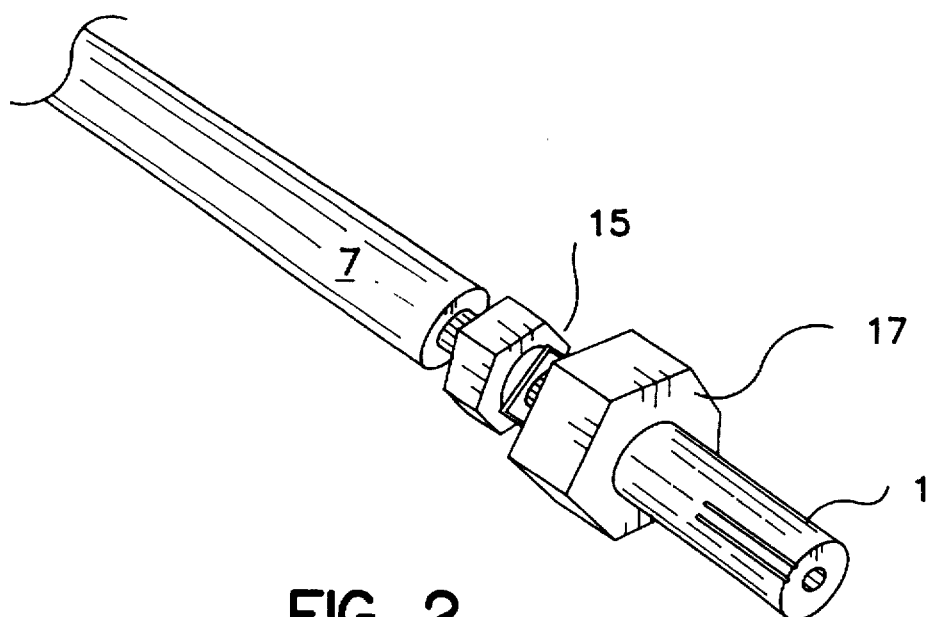
FIG. 2, is an exterior view of the hydrogen and temperature sensor probe.
Figure 3:
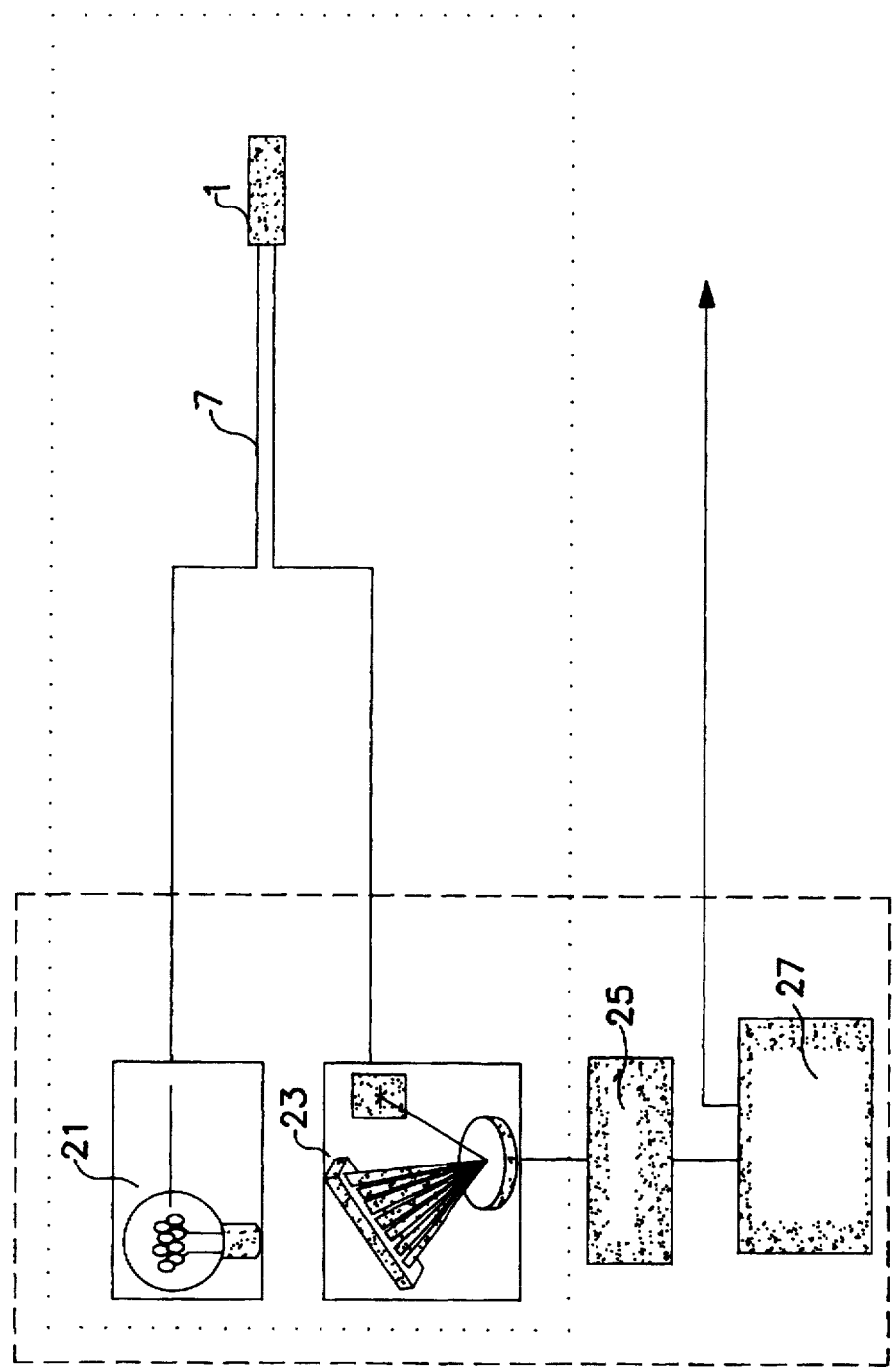
FIG. 3, is a schematic of the transmission system for communication between the sensor probe and the analysis equipment.

The preferred embodiment of the apparatus comprises a rigid sensor probe 1 that contains a lens 3 in the monitoring end that has three thin-film layers 5 of composite materials deposited on the distal end of the lens in the sensor probe, with light transmitted to and from the sensor probe by means of fiber-optic cables 7.

The sensor probe is designed to be approximately one quarter inch in diameter at the distal monitoring end where the lens 3 of quartz material is coated with three contiguous layers 5 of composite materials. The most distal or exterior layer is a coating of hydrogen permeable material 9, such as sol-gel glass, which is a porous glass that allows the diffusion of hydrogen gas with the exclusion of other reactive gases. [For an example of the sol-gel glass composition, see U.S. patent application 08/192,266, Wicks, et al. (02/07/94) now U.S. 5,637,507.] The sol-gel glass material can be replaced with a teflon coating, with either coating allowing hydrogen gas to pass into the sensor probe to the second layer of composite material 11.

The second layer of composite material 11 is composed of any reflective metal material that forms a metal hydride upon absorbing hydrogen without significant changes in the metal's reflective properties. An example of such reflective metal is a palladium alloy film, which is reflective to the light transmitted from the light source through the fiber-optic fibers.

The third layer 13 in from the distal end of the sensor probe is a layer of semi-conducting solid that is transparent above a temperature dependent minimum wavelength which is within the range of light monitored by the spectrometer analysis equipment. An example of such semi-conducting solid is zinc selenide, which is transparent to wavelengths above a minimum wavelength that depends on the temperature of the solid. The interior of the sensor probe is light transmissive, allowing light to pass to the quartz lens 3 that is positioned in front of a fiber-optic terminator connector 15. The fiber-optic cable 7 is connected to the sensor probe by the terminator connector 15, which positions two optic fibers at the base of the sensor probe 17, where the light is focused by the lens 3. The optic fibers transmit light variations from the lens and the reflective metal layer of the sensor probe, by fiber-optic cable to a spectrometer, a broad-band light source such as a tungsten-light source, and system controller devices.

The second layer, such as a palladium alloy film, is deposited by thin layer technology and consists of a reflective film between the exterior sol-gel glass or teflon coating, and the interior zinc selenide temperature sensor layer. The optical properties of the palladium film layer are altered by the presence of hydrogen absorbed from the atmosphere through the exterior layer of sol-gel glass or teflon. As the concentrations of hydrogen change, the optical properties change in the palladium film, and the intensity of the light reflected by the film into the quartz lens varies. The reflected light transmitted through the lens into the optic fibers, then through the fiber-optic cable from the palladium film to the spectrometer is analyzed for variations from which a hydrogen concentration is calculated utilizing an analog to digital converter and software developed for the sensor system.

The third innermost layer of the distal end of the sensor probe consists of a layer of semi-conducting solid that is transparent above a temperature dependent minimum wavelength, such as a layer of zinc selenide temperature sensitive material 13. The zinc selenide layer is commercially obtainable and is used for windows in NIR spectroscopy. This layer allows unimpeded passage of light to and from the reflective palladium alloy film layer 11, for wavelengths above a temperature dependent minimum wavelength. The lack of interference by the zinc selenide layer with the functioning of the palladium alloy film, along with the simultaneous functioning of the zinc selenide layer to provide temperature readings based on the location of the minimum, provides a innovative and compact sensor probe.

Two optic fibers 17 are located inside the sensor probe and positioned at the focal point of the quartz lens by the male and female connection of the swagelock reducer 19, and the fiberoptic terminator 15. The two optic fibers exit the sensor probe through the base or proximal end of the swage lock reducer. The swagelock reducer is a cylinder of stainless steel with a female connector at the proximal end of the sensor probe. The female connector 19 attaches to the male connector of the fiber-optic cable terminator 15, for secure hermetic seal of the fiber-optic cable to the proximal end of the sensor probe. The two fiber optic cables in the fiber optic terminator are positioned in front of the quartz lens at its focal point by the female-male connector 15. Light emitted from a broad-band light source, such as a tungsten-halogen source, is transmitted through one optic fiber of the fiber-optic cable 7, and is collimated by the quartz lens 3, before the light passes through the zinc selenide layer 13, is reflected off of the palladium allow film 11, passes again through the zinc selenide layer 13, and is focused on returning through the quartz lens 3, onto the second optic fiber of the fiber-optic cable 7, which carries the altered light to a spectrometer for analysis.

A broad-based light source 21, such as a tungsten-halogen lamp, generates the light for transmission by the fiber-optic cable to the sensor probe. A diode array spectrometer 23, such as a Zeiss MCS unit, analyzes the optical transmissions from the sensor probe. The spectrometer is assisted with analysis and manipulation of the optical information from the sensor probe by an analog to digital converter 25, a system controller processor 27 and associated chemometric software developed by the inventor. The above described sensor-probe containing layers of composite materials 9, 11, 13, and the quartz lens 3, the optic fibers 17, the swagelock reducer 19, the connector and fiber-optic terminator 15, fiber-optic cable 7, tungsten-halogen lamp, diode array spectrometer 21, analog to digital converter 25, system controller hardware 27 and associated chemometric software comprises the hydrogen concentration and temperature monitoring sensor system.

Although the present invention has been described in considerable detail with reference to certain preferred versions thereof, other versions are possible. For example, the exterior material of the sensor probe may be a metal such as stainless steel, or a composite material such as plastic, graphite composite, or ceramics as long the material does not transmit light. The coating of sol-gel glass can be replaced by a layer of teflon or any comparable material that is selectively permeable to hydrogen, and is located on the exterior distal end of the sensor probe.

The reflective palladium film can be replaced by any layer of metallic absorbing reflective metal material that forms a metal hydride upon absorbing hydrogen. The zinc selenide temperature sensor layer can be replaced by any semi-conducting solid that is transparent above a temperature dependent minimum wavelength.

Many variations will undoubtedly become apparent to one skilled in the art upon a reading of the above specification with reference to the drawings. Such variations, however, are within the spirit and scope of the invention as defined by the following appended claims.

What is claimed is:

1. A sensor system capable of measuring hydrogen concentrations and temperatures comprising:

a sensor probe having a rigid housing with one distal open end;

a light transparent lens inside said sensor probe with one end oriented toward the distal open end of the sensor probe and the other end of said lens oriented toward the proximal closed end of the sensor probe;

a sem-conducting solid that is transparent above a temperature dependent minimum wavelength, forming a layer on the distal end of said lens inside said sensor probe;

a reflective metal material that forms a metal hydride upon absorbing hydrogen, forming a layer on top of and contiguous with said semi-conducting solid layer inside said sensor probe;

a coating of hydrogen permeable material on top of, distal, and contiguous with said reflective metal material layer within said sensor probe;

a rigid connector at the proximal end of said sensor probe;

first and second optical fibers positioned at a focal point of the lens inside said sensor probe by a fiber-optic terminator and connector at the proximal end of said sensor probe;

a means for generating light comprising a broad-band light source;

a fiber-optic cable comprising said first and second optical fibers, said first optical fiber connecting the sensor probe to said source of broad-band light;

a controlling processor;

a means for analysis of light information from said sensor probe comprising a spectrometer; and a means for transmission of light from said reflective metal material layer and said semi-conducting solid layer to said means for analysis.

2. The sensor system capable of measuring hydrogen concentrations and temperatures as described in claim 1, wherein said sensor probe is constructed of a swagelock connector with one distal end open and the other proximal end closed with a female connector.

3. The sensor system capable of measuring hydrogen concentrations and temperatures as described in claim 1, wherein said lens is composed of quartz.

4. The sensor system capable of measuring hydrogen concentrations and temperatures as described in claim 1, wherein said pair of optical fibers extend close to and in alignment with said lens inside said sensor probe.

5. The sensor system capable of measuring hydrogen concentrations and temperatures as described in claim 1, wherein said semi-conducting solid that is transparent above a temperature dependent minimum wavelength comprises a zinc selenide temperature sensor layer on the distal end of said light transparent lens, said temperature sensor layer being transparent to broad-based light above a minimum wavelength.

6. The sensor system capable of measuring hydrogen concentrations and temperatures as described in claim 1, wherein said coating is selected from the group consisting of sol-gel glass and teflon, said coating being located on top of and contiguous with said reflective metal material layer inside the distal end of said sensor probe.

7. The sensor system capable of measuring hydrogen concentrations and temperatures as described in claim 1, said rigid connector comprising a female connector of a swagelock reducer which connects to said fiber-optic terminator and connector at the proximal end of said sensor probe.

8. The sensor system capable of measuring hydrogen concentrations and temperatures as described in claim 1, said means for generating light comprising a quartz-halogen light source.

9. The sensor system capable of measuring hydrogen concentrations and temperatures as described in claim 1, said controlling processor including an analog-to-digital converter.

10. The sensor system capable of measuring hydrogen concentrations and temperatures as described in claim 1, said means for generating light comprising a tungsten-halogen light source, said light source being connected by said first optical fiber to said sensor probe.

11. The sensor system capable of measuring hydrogen concentrations and temperatures as described in claim 1, wherein said reflective metal material that forms a metal hydride upon absorbing hydrogen comprises a palladium alloy film layer on top of and contiguous with said semi-conducting solid layer inside the distal end of said sensor probe.

12. The sensor system as described in claim 11, wherein said palladium alloy layer is reflective to light passing through said lens and through said semi-conducting solid layer inside said sensor probe.

13. A sensor device for use in measuring hydrogen concentrations and temperatures comprising:

a sensor probe having a rigid housing with one distal open end;

a light transparent lens inside said sensor probe with one end oriented toward the distal open end of the sensor probe and the other end of said lens oriented toward the proximal closed end of the sensor probe;

a semi-conducting solid that is transparent above a temperature dependent minimum wavelength, forming a layer on the distal end of said lens inside said sensor probe;

a reflective metal material that forms a metal hydride upon absorbing hydrogen, forming a layer on top of and contiguous with said semi-conducting solid layer inside said sensor probe;

a coating of hydrogen permeable material on top of, distal, and contiguous with said reflective metal material layer within said sensor probe;

a rigid connector at the proximal end of said sensor probe; and a pair of optical fibers positioned at a focal point of the lens inside said sensor probe by a fiber-optic terminator and connector at the proximal end of said sensor probe.

* * * * *